United States Patent
Wei et al.

(10) Patent No.: US 12,220,481 B2
(45) Date of Patent: Feb. 11, 2025

(54) BUCCAL MICRO-EFFERVESCENT TABLET AND PREPARATION METHOD THEREOF

(71) Applicant: BYHEALTH CO., LTD., Guangdong (CN)

(72) Inventors: Jingqiang Wei, Guangdong (CN);
Yuanying Huang, Guangdong (CN);
Xuguang Zhang, Guangdong (CN);
Meijuan Liu, Guangdong (CN);
Wenqiong Mai, Guangdong (CN)

(73) Assignee: BYHEALTH CO., LTD., Guangdong (CN)

( * ) Notice: Subject to any disclaimer, the term of this patent is extended or adjusted under 35 U.S.C. 154(b) by 602 days.

(21) Appl. No.: 17/286,322

(22) PCT Filed: Jun. 26, 2019

(86) PCT No.: PCT/CN2019/092936
§ 371 (c)(1),
(2) Date: Apr. 16, 2021

(87) PCT Pub. No.: WO2020/078036
PCT Pub. Date: Apr. 23, 2020

(65) Prior Publication Data
US 2022/0000770 A1    Jan. 6, 2022

(30) Foreign Application Priority Data

Oct. 17, 2018  (CN) .......................... 201811208708.0

(51) Int. Cl.

| | |
|---|---|
| A61K 9/00 | (2006.01) |
| A23L 5/30 | (2016.01) |
| A23L 27/00 | (2016.01) |
| A23L 27/30 | (2016.01) |
| A23L 29/00 | (2016.01) |
| A23L 29/30 | (2016.01) |
| A23L 33/15 | (2016.01) |
| A23L 33/155 | (2016.01) |
| A23P 10/28 | (2016.01) |
| A61K 9/20 | (2006.01) |
| A61K 9/46 | (2006.01) |
| A61K 31/375 | (2006.01) |

(52) U.S. Cl.
CPC .............. *A61K 9/0056* (2013.01); *A23L 5/30* (2016.08); *A23L 27/36* (2016.08); *A23L 33/155* (2016.08); *A61K 9/2009* (2013.01); *A61K 9/2018* (2013.01); *A61K 9/2095* (2013.01)

(58) Field of Classification Search
CPC ............ A23V 2002/00; A23V 2200/30; A23V 2250/032; A23V 2250/1614; A23V 2250/1628; A23V 2250/2482; A23V 2250/262; A23V 2250/264; A23V 2250/612; A23V 2250/6412; A23V 2250/6416; A23V 2250/642; A23V 2250/708; A23P 10/28; A61K 9/0056; A61K 9/2009; A61K 9/2018; A61K 9/2095; A61K 31/375; A61K 9/0007; A23L 27/36; A23L 33/15; A23L 33/155; A23L 5/30; A23L 27/00; A23L 27/32; A23L 27/33; A23L 29/015; A23L 29/035; A23L 29/30
See application file for complete search history.

(56) References Cited

U.S. PATENT DOCUMENTS

| | | | |
|---|---|---|---|
| 5,330,760 | A | 7/1994 | Walton |
| 6,235,318 | B1 | 5/2001 | Lombardy, Jr. et al. |
| 6,242,002 | B1 | 6/2001 | Tritthart et al. |
| 6,428,770 | B1 | 8/2002 | Kayane et al. |
| 8,753,611 | B2 | 6/2014 | Eichman et al. |
| 2002/0127184 | A1 | 9/2002 | Selim |
| 2011/0014132 | A1 | 1/2011 | Liu |
| 2014/0371174 | A1* | 12/2014 | Stella ................ A61K 47/12 |
| | | | 514/63 |

FOREIGN PATENT DOCUMENTS

| | | | |
|---|---|---|---|
| CN | 1559423 | A | 1/2005 |
| CN | 1682697 | A | 10/2005 |
| CN | 101919801 | A | 12/2010 |
| CN | 103062295 | A | 5/2013 |
| CN | 107149077 | A | 9/2017 |
| CN | 109303334 | A | 2/2019 |
| EP | 0 737 473 | A1 * | 10/1996 ............... A61K 9/46 |

(Continued)

OTHER PUBLICATIONS

Kumar et al.; Journal of Applied Pharmaceutical Sciences 01(05); 2011; pp. 50-58. Published Jul. 30, 2011.*
Examination Report No. 1 issued Sep. 27, 2021 in corresponding Australian Patent Application No. 2019362348.
International Search Report mailed Oct. 8, 2019 in corresponding International Patent Application No. PCT/CN2019/092936.

*Primary Examiner* — Jeffrey T. Palenik
(74) *Attorney, Agent, or Firm* — MEDLER FERRO WOODHOUSE & MILLS PLLC

(57) ABSTRACT

Provided is a buccal micro-effervescent tablet and preparation method thereof. The buccal micro-effervescent tablet includes a nutrient, a sugar alcohol, an acid source, an alkali source, magnesium stearate, an essence and a sweetening agent, wherein the sugar alcohol is lactose, maltitol, sorbitol, isomaltitol, mannitol, erythritol or any combination thereof and the sweetening agent is sucralose, aspartame, stevioside, fructose, granulated sugar, mogroside or any combination thereof. The micro-effervescent tablet is configured to cause a micro effervescence reaction under the action of saliva in mouth.

5 Claims, No Drawings

(56) References Cited

FOREIGN PATENT DOCUMENTS

| | | |
|---|---|---|
| EP | 2 424 502 B1 * 4/2010 | ............... A61K 9/00 |
| JP | H05-500956 A 2/1993 | |
| JP | 2002-540141 A 11/2002 | |
| JP | 2018-83763 A 5/2018 | |
| WO | 91/04757 A1 4/1991 | |
| WO | 00/57858 A1 10/2000 | |
| WO | 2018/117855 A1 6/2018 | |

* cited by examiner

BUCCAL MICRO-EFFERVESCENT TABLET AND PREPARATION METHOD THEREOF

TECHNICAL FIELD

The invention relates to the field of health food preparation, in particular to a buccal micro-effervescent tablet and preparation method thereof.

BACKGROUND ART

Vitamins are a class of trace organic substances that must be obtained from food for humans and animals to maintain normal physiological functions, and play an important role in the growth, metabolism, and development of the human body. These substances are neither materials constituting body tissues nor sources of energy in the body, but rather are modulating substances that play an important role in substance metabolism. The human body is like a very complex chemical plant, wherein various biochemical reactions are continuously carried out, and the reactions are closely related to the catalytic action of enzymes. For the enzyme to be active, it is required to have a coenzyme involved. Many vitamins are known to be the coenzymes of enzymes or the constituent molecules of the coenzyme. Thus, vitamins are important substances for maintaining and regulating the normal metabolism of the body.

The effervescent tablet is a new health food and pharmaceutical preparation in China, which contains organic acid and basic (bi)carbonate as effervescent disintegrant. The effervescent tablet is placed into water, and the organic acid reacts with the basic (bi)carbonate instantly to generate and release a large amount of carbon dioxide gas, like boiling. As compared with the common tablets, the effervescent tablets have the following advantages: (1) convenient administration and fast action; (2) good taste and patient compliance, and being particularly suitable for children, the elderly and patients with difficulty in swallowing solid preparations; (3) rapidly disintegrating within 1-5 mins; (4) high bioavailability, and being capable of improving the clinical effect; (5) slightly acidic property, which can increase the stability and the solubility of some drugs; (6) being suitable to be used for preventing and treating oral diseases, vaginal diseases and the like because a large amount of foams generated by disintegration can increase the direct contact between the drug and the diseased region thereby for the effervescent tablet to exert better clinical effect; (7) being easy to carry, transport and store.

The effervescent tablet prepared from single vitamin or various vitamins is popular with consumers. However, the effervescent tablet needs to be dissolved in water before being taken, and in the absence of drinking equipment or drinking water, taking effervescent tablets will cause many inconveniences to consumers.

SUMMARY OF THE INVENTION

In order to solve the problems in the prior art, the present application provides a buccal micro-effervescent tablet and preparation method thereof. The buccal micro-effervescent tablet is a new preparation form, can cause micro effervescence under the action of saliva in mouth, has good taste and strong experience, and thus the following inventions are provided.

In an aspect, the present application provides a buccal micro-effervescent tablet comprising a nutrient, a sugar alcohol, an acid source, an alkali source, magnesium stearate, an essence, and a sweeting agent, wherein, the sugar alcohol is lactose, maltitol, sorbitol, isomaltitol, mannitol, erythritol or any combination thereof, the sweetening agent is sucralose, aspartame, stevioside, fructose, granulated sugar, mogroside or any combination thereof, the buccal micro-effervescent tablet comprises in parts by weight: 1-30 parts of a nutrient, 10-80 parts of a sugar alcohol, 10-40 parts of an acid source, 10-40 parts of an alkali source, 0.1-3 parts of a magnesium stearate, 1-5 parts of an essence and 0.1-3 parts of a sweetening agent, wherein the weight ratio of the acid source in the buccal micro-effervescent tablet is not more than 19% (e.g., 1%-5%, 5%-10%, 10%-15%, or 15%-19%), the weight ratio of the alkali source in the buccal micro-effervescent tablet is not more than 18% (e.g., 1%-5%, 5%-10%, 10%-15% or 15%-18%).

In some embodiments, the buccal micro-effervescent tablet comprises 48-63 parts of a sugar alcohol in parts by weight. In some embodiments, the buccal micro-effervescent tablet comprises 0.8-1.5 parts of a magnesium stearate in parts by weight.

In some embodiments, the buccal micro-effervescent tablet comprises 11-19 parts of an acid source in parts by weight.

In some embodiments, the buccal micro-effervescent tablet comprises 11-18 parts of an alkali source in parts by weight.

In some embodiments, the buccal micro-effervescent tablet comprises in parts by weight:

8-12 parts of a nutrient, 10-80 parts of a sugar alcohol, 10-40 parts of an acid source, 10-40 parts of an alkali source, 0.1-3 parts of a magnesium stearate, 1-5 parts of an essence and 0.1-3 parts of a sweetening agent.

In some embodiments, the buccal micro-effervescent tablet comprises in parts by weight:

10-11 parts of a nutrient, 48-63 parts of a sugar alcohol, 11-19 parts of an acid source, 11-18 parts of an alkali source, 0.8-1.5 parts of a magnesium stearate, 1.5-2 parts of an essence and 0.2-1.2 parts of a sweetening agent.

In some embodiments, the nutrient is a vitamin.

In some embodiments, the vitamin is vitamin A, vitamins B, vitamin C, vitamin D, vitamin E, vitamin K, or any combination thereof.

In some embodiments, the buccal micro-effervescent tablet of the present invention comprises vitamin A. Vitamin A, an anti-xerophthalmia vitamin, also known as a cosmetic vitamin, is fat-soluble. Vitamin A is not a single compound but a series of retinol (also known as vitamin A alcohol or rosin oil) derivatives. Vitamin A can be used for preventing or treating nyctalopia.

In some embodiments, the buccal micro-effervescent tablet of the present invention comprises vitamin $B_1$. Vitamin $B_1$, also known as thiamine, is also called anti-beriberi factor, anti-neuritis factor, and the like, is a water-soluble vitamin. Vitamin $B_1$ can be used for preventing or treating seborrheic dermatitis or eczema.

In some embodiments, the buccal micro-effervescent tablet of the present invention comprises vitamin $B_2$. Vitamin $B_2$, also known as riboflavin, is also called vitamin G, and is water-soluble. Vitamin $B_2$ can be used for preventing or treating inflammation of mouth and tongue (aphthous ulcer).

In some embodiments, the buccal micro-effervescent tablet of the present invention comprises vitamin C. Vitamin C, as known as ascorbic acid, is water soluble and can be used for preventing or treating scurvy.

In some embodiments, the buccal micro-effervescent tablet of the present invention comprises vitamin D. Vitamin D, as known as calciferol, is fat-soluble and can be used for preventing or treating rickets.

In some embodiments, the sugar alcohol is lactose, maltitol, sorbitol, isomaltitol or any combination thereof.

In some embodiments, the sugar alcohol is lactose and maltitol. In some embodiments, the ratio of lactose to maltitol is 1:0.2-4.5 (e.g., 1:0.2, 1:2.2, or 1:4.5) in parts by weight.

In some embodiments, the sugar alcohol is sorbitol and lactose. In some embodiments, the ratio of sorbitol to lactose is 1:0.39-4.2 (e.g., 1:0.39, 1:0.74, 1:0.85 or 1:4.2) in parts by weight.

In some embodiments, the sugar alcohol is isomaltitol and lactose. In some embodiments, the ratio of isomaltitol to lactose is 1:0.46-1.6 in parts by weight.

In some embodiments, the sweetening agent is sucralose, aspartame, stevioside, or any combination thereof.

In some embodiments, the acid source is citric acid, tartaric acid, fumaric acid, malic acid, or any combination thereof, the alkali source is sodium bicarbonate, sodium carbonate, potassium bicarbonate, potassium carbonate or any combination thereof.

In some embodiments, the buccal micro-effervescent tablet further comprises a silicon dioxide, wherein the weight ratio of the silicon dioxide in the buccal micro-effervescent tablet is 0.1%-1%.

In some embodiments, the buccal micro-effervescent tablet further comprises a silicon dioxide, wherein the weight ratio of the silicon dioxide in the buccal micro-effervescent tablet is 0.5%.

In some embodiments, the buccal micro-effervescent tablet of the present invention comprises: a lactose, a maltitol, a vitamin C, an anhydrous citric acid, a sodium bicarbonate, an essence, a sucralose, an aspartame, a stevioside, and a magnesium stearate, optionally further comprises a silicon dioxide. In some embodiments, the buccal micro-effervescent tablet of the present invention comprises in parts by weight: 9.8-48.8 parts (e.g., 9.8-16.1 parts or 16.1-48.8 parts) of a lactose, 10-42.5 parts (e.g., 10-35 parts or 35-42.5 parts) of a maltitol, 10-10.5 parts of a vitamin C, 14-17.5 parts of an anhydrous citric acid, 14-16.25 parts of a sodium bicarbonate, 1.7-2 parts of an essence, 0.025-0.03 parts of a sucralose, 0.12-0.6 parts of an aspartame, 0.05-0.3 parts of a stevioside, 0.8-1.5 parts (such as 0.8-1 or 1-1.5 parts) of a magnesium stearate, and optionally further comprises 0.1-1 parts (such as 0.1-0.5 parts or 0.5-1 parts) of a silicon dioxide.

In some embodiments, the buccal micro-effervescent tablet of the present invention comprises: a maltitol, a vitamin C, an anhydrous citric acid, a sodium bicarbonate, an essence, a sucralose, an aspartame, a stevioside, a magnesium stearate and a silicon dioxide. In some embodiments, the buccal micro effervescent tablet of the present invention comprises in parts by weight: 10 to 80 parts (e.g., 10-62.7 parts or 62.7-80 parts) of a maltitol, 1-30 parts (e.g., 1-10.5 parts or 10.5-30 parts) of a vitamin C, 10-40 parts (e.g., 10-11.3 parts or 11.3-40 parts) of an anhydrous citric acid, 10-40 parts (e.g., 10-11.25 parts or 11.25-40 parts) of a sodium hydrogencarbonate, 1 to 5 parts (e.g., 1 to 1.5 parts or 1.5 to 5 parts) of an essence, 0.1-3 parts of a combination of a sucralose, a stevioside and an aspartame (e.g., 0.025-0.03 parts of a sucralose, 0.3-0.4 parts of a stevioside, 0.4-0.5 parts of an aspartame), 0.1 to 3 parts (e.g., 0.1-1.5 parts or 1.5-3 parts) of a magnesium stearate, 0.1 to 1 parts (e.g., 0.1 to 0.5 parts or 0.5 to 1 part) of a silicon dioxide.

In some embodiments, the buccal micro-effervescent tablet of the present invention comprises: a maltitol, a lactose, a vitamin C, an anhydrous citric acid, a sodium bicarbonate, an essence, a sucralose, an aspartame, a stevioside, and a magnesium stearate, optionally further comprises a silicon dioxide. In some embodiments, the buccal micro effervescent tablet of the present invention comprises in parts by weight: 10-35 parts (e.g., 10-30 parts or 30-35 parts) of a sorbitol, 13.6-41.7 parts (e.g., 13.6-22.3 parts, 22.3-25.4 parts or 25.4-41.6 parts) of a lactose, 10-10.5 parts of a vitamin C, 15-18.75 parts (e.g., 15-17.5 parts or 17.5-18.75 parts) of an anhydrous citric acid, 15-17.5 parts (e.g., 15-16.25 parts or 16.25-17.5 parts) of a sodium bicarbonate, 1-5 parts (e.g., 1-1.7 parts or 1.7-5 parts) of an essence, 0.1-3 parts of a combination of a sucralose, a stevioside and an aspartame (e.g., 0.025-0.03 parts of a sucralose, 0.6-0.7 parts of an aspartame, 0.3-0.4 parts of a stevioside), 0.8-1.5 parts of a magnesium stearate, and optionally further comprises 0.1 to 1 parts (e.g., 0.1-0.5 parts or 0.5-1 parts) of a silicon dioxide.

In some embodiments, the buccal micro-effervescent tablet of the present invention comprises: a lactose, a vitamin C, an anhydrous citric acid, a sodium bicarbonate, an essence, a sucralose, an aspartame, a stevioside, a magnesium stearate and a silicon dioxide. In some embodiments, the buccal micro effervescent tablet of the present invention comprises in parts by weight: 10 to 80 parts (e.g., 10-59.4 parts or 59.4-80 parts) of a lactose, 1-30 parts (e.g., 1-10.5 parts or 10.5-30 parts) of a vitamin C, 10-40 parts (e.g., 10-15.25 parts or 15.25-40 parts) of an anhydrous citric acid, 10-40 parts (e.g., 10-11.25 parts or 11.25-40 parts) of a sodium bicarbonate, 1 to 5 parts (e.g., 1 to 1.5 parts or 1.5 to 5 parts) of an essence, 0.1-3 parts of a combination of a sucralose, a stevioside and an aspartame (e.g., 0.025-0.03 parts of a sucralose, 0.3-0.4 parts of a stevioside, 0.8-0.9 parts of an aspartame), 0.1 to 3 parts (e.g., 0.1-0.5 parts or 0.5-3 parts) of a magnesium stearate, 0.1 to 1 parts (e.g., 0.1 to 0.5 parts or 0.5 to 1 part) of a silicon dioxide.

In some embodiments, the buccal micro-effervescent tablet of the present invention comprises: an isomaltitol, a lactose, a vitamin C, an anhydrous citric acid, a sodium bicarbonate, an essence, a sucralose, an aspartame, a stevioside, and a magnesium stearate, optionally further comprises a silicon dioxide. In some embodiments, the buccal micro effervescent tablet of the present invention comprises in parts by weight: 20-35 parts of an isomaltitol, 16.075-32.275 parts of a lactose, 1-30 parts (e.g., 1-10.5 parts or 10.5-30 parts) of a vitamin C, 10-40 parts (e.g., 10-17.5 parts or 17.5-40 parts) of an anhydrous citric acid, 10-40 parts (e.g., 10-16.25 parts or 16.25-40 parts) of a sodium bicarbonate, 1-5 parts (e.g., 1-1.7 parts or 1.7-5 parts) of an essence, 0.1-3 parts of a combination of a sucralose, a stevioside and an aspartame (e.g., 0.025-0.03 parts of a sucralose, 0.35-0.4 parts of a stevioside, 0.6-0.7 parts of an aspartame), 0.8-1.5 parts of a magnesium stearate, and optionally further comprises 0.1-1 parts (e.g., 0.1-0.5 parts or 0.5-1 parts) of a silicon dioxide.

In some embodiments, the buccal micro-effervescent tablet of the present invention comprises: an isomaltitol, a vitamin C, an anhydrous citric acid, a sodium bicarbonate, an essence, a sucralose, an aspartame, a stevioside, a magnesium stearate and a silicon dioxide. In some embodiments, the buccal micro effervescent tablet of the present invention comprises in parts by weight: 10 to 80 parts (e.g., 10-51.35 parts or 51.35-80 parts) of an isomaltitol, 1-30 parts (e.g., 1-10.5 parts or 10.5-30 parts) of a vitamin C, 10-40 parts (e.g., 10-17.5 parts or 17.5-40 parts) of an anhydrous citric acid, 10-40 parts (e.g., 10-16.25 parts or 16.25-40 parts) of a sodium hydrogencarbonate, 1 to 5 parts (e.g., 1 to 1.7 parts or 1.7 to 5 parts) of an essence, 0.1-3 parts of a combination of a sucralose, a stevioside and an aspartame (e.g., 0.025-0.03 parts of a sucralose, 0.3-0.4 parts of a stevioside, 0.6-0.7 parts of an aspartame), 0.1 to 3 parts (e.g., 0.1-1.5 parts or 1.5-3 parts) of a magnesium stearate, 0.1 to 1 part (e.g., 0.1 to 0.5 parts or 0.5 to 1 part) of silicon dioxide.

In some embodiments, the buccal micro-effervescent tablet of the present invention may comprise other nutrients in addition to vitamins, for example, blueberry extract, zeaxanthin, lutein, lutein ester, taurine, caffeine, guarana, r-aminobutyric acid, tea theanine, melatonin, milk mineral, grape seed extract, olive fruit extract, collagen powder, elastic collagen, probiotics, ferment, dietary fiber, prebiotics, phosphatidylserine, DHA and the like.

In another aspect, the present application provides a method for preparing a buccal micro-effervescent tablet of the present invention, comprising the steps of: mixing a nutrient, a sugar alcohol, an acid source, an alkali source, a magnesium stearate, an essence and a sweetening agent to obtain a mixture, and compressing the mixture into a tablet.

The present application also relates to the following technical solutions:

Technical solution 1: a buccal micro-effervescent tablet characterized in that the buccal micro-effervescent tablet comprises a nutrient, a sugar alcohol, an acid source, an alkali source, a magnesium stearate, an essence and a sweetening agent, wherein the sugar alcohol is selected from the group consisting of lactose, maltitol, sorbitol, isomaltitol, mannitol, erythritol, and any combination of them, the sweetening agent is selected from the group consisting of sucralose, aspartame, stevioside, fructose, granulated sugar, mogroside, and any combination of them, the buccal micro-effervescent tablet comprises in parts by weight:

1-30 parts of a nutrient, 10-80 parts of a sugar alcohol, 10-40 parts of an acid source, 10-40 parts of an alkali source, 0.1-3 parts of a magnesium stearate, 1-5 parts of an essence and 0.1-3 parts of a sweetening agent, the weight ratio of the acid source in the buccal micro-effervescent tablet is not more than 19%, the weight ratio of the alkali source in the buccal micro-effervescent tablet is not more than 18%.

Technical solution 2: the buccal micro-effervescent tablet according to technical solution 1, characterized in that the buccal micro-effervescent tablet comprises in parts by weight:

8-12 parts of a nutrient, 10-80 parts of a sugar alcohol, 10-40 parts of an acid source, 10-40 parts of an alkali source, 0.1-3 parts of a magnesium stearate, 1-5 parts of an essence and 0.1-3 parts of a sweetening agent.

Technical solution 3: the buccal micro-effervescent tablet according to technical solution 1, characterized in that the buccal micro-effervescent tablet comprises in parts by weight:

10-11 parts of a nutrient, 48-63 parts of a sugar alcohol, 11-19 parts of an acid source, 11-18 parts of an alkali source, 0.8-1.5 parts of a magnesium stearate, 1.5-2 parts of an essence and 0.2-1.2 parts of a sweetening agent.

Technical solution 4: the buccal micro-effervescent tablet according to technical solution 1, characterized in that the nutrient is a vitamin.

Technical solution 5: the buccal micro-effervescent tablet according to technical solution 4, characterized in that the vitamin is one or more selected from the group consisting of vitamin A, vitamins B, vitamin C, vitamin D, vitamin E and vitamin K.

Technical solution 6: the buccal micro-effervescent tablet according to technical solution 1, characterized in that the sugar alcohol is selected from the group consisting of lactose, maltitol, sorbitol, isomaltitol, and any combination of them.

Technical solution 7: the buccal micro-effervescent tablet according to technical solution 1, characterized in that the sweetening agent is selected from the group consisting of sucralose, aspartame, stevioside, and any combination of them.

Advantageous Effects

Compared with the conventional effervescent tablet, the buccal micro-effervescent tablet of the present invention slowly generates a few small bubbles upon contact with water, and does not generate violent effervescence. Therefore, the micro-effervescent tablet of the present invention can be directly placed in mouth for buccal administration, is convenient to take, which can avoid safety risk caused by a large amount of carbon dioxide gas generated in mouth. Meanwhile, the micro-effervescent tablet of the present invention can also be dissolved in water and can be taken according to a method similar to that of the conventional effervescent tablet.

Furthermore, by selecting the components in the micro-effervescent tablet and adjusting the proportion of the components, the invention solves the problem of serious moisture absorption of the effervescent tablet in the production process or acceleration test.

SPECIFIC MODES FOR CARRYING OUT THE INVENTION

The embodiments of the invention are illustrated by way of the following examples. However, a person skilled in the art understands that the following examples are provided for the purpose of describing the invention and shall not be regarded as defining the scope of the invention. The raw materials or auxiliary materials used in the examples are all commercially available.

Example 1

In parts by weight, the buccal micro-effervescent tablet of the example had the components listed in the prescription as follows.

| | |
|---|---|
| lactose | 48.8 |
| maltitol | 10 |
| vitamin C | 10 |
| anhydrous citric acid | 14 |
| sodium bicarbonate | 14 |
| edible essence | 2 |
| sucralose | 0.03 |
| aspartame | 0.12 |
| stevioside | 0.05 |
| magnesium stearate | 1 |

Process:
1. Weighing and Preparing

All the materials were weighed according to the prescription, and crushed, premixed or sieved selectively according to the properties of the materials.

2. Mixing

Nutrients, sweetening agents, sugar alcohols, citric acid, sodium bicarbonate, essences, and magnesium stearate were placed in the mixer, and mixed until the mixture was uniform in color and texture.

3. Compressing

The mixture was compressed into tablets and the size of tablet was 40 mg.

Example 2

In parts by weight, the buccal micro-effervescent tablet of the example had the components listed in the prescription as follows.

| | |
|---|---|
| lactose | 16.125 |
| maltitol | 35 |
| vitamin C | 10.5 |
| anhydrous citric acid | 17.5 |
| sodium bicarbonate | 16.25 |
| edible essence | 1.7 |
| sucralose | 0.025 |
| aspartame | 0.6 |
| stevioside | 0.3 |
| magnesium stearate | 1.5 |
| silicon dioxide | 0.5 |

The Process including mixing and compressing was similar to that in Example 1.

Example 3

In parts by weight, the buccal micro-effervescent tablet of the example had the components listed in the prescription as follows.

| | |
|---|---|
| lactose | 9.825 |
| maltitol | 42.5 |
| vitamin C | 10.5 |
| anhydrous citric acid | 17.5 |
| sodium bicarbonate | 16.25 |
| edible essence | 1.7 |
| sucralose | 0.025 |
| aspartame | 0.6 |
| stevioside | 0.3 |
| magnesium stearate | 0.8 |

The Process including mixing and compressing was similar to that in Example 1.

Example 4

In parts by weight, the buccal micro-effervescent tablet of the example had the components listed in the prescription as follows.

| | |
|---|---|
| maltitol | 62.725 |
| vitamin C | 10.5 |
| anhydrous citric acid | 11.3 |
| sodium bicarbonate | 11.25 |
| edible essence | 1.5 |
| sucralose | 0.025 |
| aspartame | 0.4 |
| stevioside | 0.3 |
| magnesium stearate | 1.5 |
| silicon dioxide | 0.5 |

The Process including mixing and compressing was similar to that in Example 1.

Example 5

In parts by weight, the buccal micro-effervescent tablet of the example had the components listed in the prescription as follows.

| | |
|---|---|
| sorbitol | 10 |
| lactose | 41.625 |
| vitamin C | 10 |
| anhydrous citric acid | 17.5 |
| sodium bicarbonate | 16.25 |
| edible essence | 1.7 |
| sucralose | 0.025 |
| aspartame | 0.6 |
| stevioside | 0.3 |
| magnesium stearate | 1.5 |
| silicon dioxide | 0.5 |

The Process including mixing and compressing was similar to that in Example 1.

Example 6

In parts by weight, the buccal micro-effervescent tablet of the example had the components listed in the prescription as follows.

| | |
|---|---|
| sorbitol | 30 |
| lactose | 25.375 |
| vitamin C | 10 |
| anhydrous citric acid | 15 |
| sodium bicarbonate | 15 |
| essence | 1.7 |
| sucralose | 0.025 |
| aspartame | 0.6 |
| stevioside | 0.3 |
| magnesium stearate | 1.5 |
| silicon dioxide | 0.5 |

The Process including mixing and compressing was similar to that in Example 1.

Example 7

In parts by weight, the buccal micro-effervescent tablet of the example had the components listed in the prescription as follows.

| | |
|---|---|
| sorbitol | 30 |
| lactose | 22.325 |
| vitamin C | 10.5 |
| anhydrous citric acid | 17.5 |
| sodium bicarbonate | 16.25 |
| essence | 1.7 |
| sucralose | 0.025 |
| aspartame | 0.6 |
| stevioside | 0.3 |
| magnesium stearate | 0.8 |

The Process including mixing and compressing was similar to that in Example 1.

Example 8

In parts by weight, the buccal micro-effervescent tablet of the example had the components listed in the prescription as follows.

| | |
|---|---|
| sorbitol | 35 |
| lactose | 13.625 |
| vitamin C | 10.5 |
| anhydrous citric acid | 18.75 |
| sodium bicarbonate | 17.5 |
| essence | 1.7 |

-continued

| | |
|---|---|
| sucralose | 0.025 |
| aspartame | 0.6 |
| stevioside | 0.3 |
| magnesium stearate | 1.5 |
| silicon dioxide | 0.5 |

The Process including mixing and compressing was similar to that in Example 1.

Example 9

In parts by weight, the buccal micro-effervescent tablet of the example had the components listed in the prescription as follows.

| | |
|---|---|
| lactose | 59.375 |
| vitamin C | 10.5 |
| anhydrous citric acid | 15.25 |
| sodium bicarbonate | 11.25 |
| essence | 1.5 |
| sucralose | 0.025 |
| aspartame | 0.8 |
| stevioside | 0.3 |
| magnesium stearate | 0.5 |
| silicon dioxide | 0.5 |

The Process including mixing and compressing was similar to that in Example 1.

Example 10

In parts by weight, the buccal micro-effervescent tablet of the example had the components listed in the prescription as follows.

| | |
|---|---|
| isomaltitol | 20 |
| lactose | 32.275 |
| vitamin C | 10.5 |
| anhydrous citric acid | 17.5 |
| sodium bicarbonate | 16.25 |
| essence | 1.7 |
| sucralose | 0.025 |
| aspartame | 0.6 |
| stevioside | 0.35 |
| magnesium stearate | 0.8 |

The Process including mixing and compressing was similar to that in Example 1.

Example 11

In parts by weight, the buccal micro-effervescent tablet of the example had the components listed in the prescription as follows.

| | |
|---|---|
| isomaltitol | 35 |
| lactose | 16.075 |
| vitamin C | 10.5 |
| anhydrous citric acid | 17.5 |
| sodium bicarbonate | 16.25 |
| essence | 1.7 |
| sucralose | 0.025 |
| aspartame | 0.6 |
| stevioside | 0.35 |
| magnesium stearate | 1.5 |
| silicon dioxide | 0.5 |

The Process including mixing and compressing was similar to that in Example 1.

Example 12

In parts by weight, the buccal micro-effervescent tablet of the example had the components listed in the prescription as follows.

| | |
|---|---|
| isomaltitol | 51.35 |
| vitamin C | 10.5 |
| anhydrous citric acid | 17.5 |
| sodium bicarbonate | 16.25 |
| essence | 1.7 |
| sucralose | 0.025 |
| Aspartame | 0.6 |
| stevioside | 0.3 |
| magnesium stearate | 1.5 |
| silicon dioxide | 0.5 |

The Process including mixing and compressing was similar to that in Example 1.

Comparative Example 1

In parts by weight, the buccal micro-effervescent tablet of the comparative example had the components listed in the prescription as follows.

| | |
|---|---|
| isomaltitol | 34.1 |
| vitamin C | 10.5 |
| anhydrous citric acid | 27 |
| sodium bicarbonate | 24 |
| essence | 1.7 |
| sucralose | 0.025 |
| aspartame | 0.6 |
| stevioside | 0.3 |
| magnesium stearate | 1.5 |
| silicon dioxide | 0.5 |

The process included mixing and compressing, and the size of tablet was 4 g.

Comparative Example 2

In parts by weight, the buccal micro-effervescent tablet of the comparative example had the components listed in the prescription as follows.

| | |
|---|---|
| isomaltitol | 27.1 |
| vitamin C | 10.5 |
| anhydrous citric acid | 30 |
| sodium bicarbonate | 28 |
| essence | 1.7 |
| sucralose | 0.025 |
| aspartame | 0.6 |
| stevioside | 0.3 |
| magnesium stearate | 1.5 |
| silicon dioxide | 0.5 |

The process included mixing and compressing.

Comparative Example 3

In parts by weight, the buccal micro-effervescent tablet of the comparative example had the components listed in the prescription as follows.

| | |
|---|---|
| lactose | 16.125 |
| microcrystalline cellulose | 35 |
| vitamin C | 10.5 |
| anhydrous citric acid | 17.5 |
| sodium bicarbonate | 16.25 |
| edible essence | 1.7 |
| sucralose | 0.025 |
| aspartame | 0.6 |
| stevioside | 0.3 |
| magnesium stearate | 1.5 |
| silicon dioxide | 0.5 |

The process included mixing and compressing.

Comparative Example 4

In parts by weight, the buccal micro-effervescent tablet of the comparative example had the components listed in the prescription as follows.

| | |
|---|---|
| lactose | 16.35 |
| maltitol | 35 |
| vitamin C | 10.5 |
| anhydrous citric acid | 17.5 |
| sodium bicarbonate | 16.25 |
| edible essence | 1.7 |
| aspartame | 0.5 |
| stevioside | 0.2 |
| magnesium stearate | 1.5 |
| silicon dioxide | 0.5 |

The process included mixing and compressing.

Test Example 1

On the basis that the sugar alcohol was a combination of maltitol and lactose, the buccal micro-effervescent tablets of vitamin C were prepared by adjusting the ratio of maltitol and lactose. The prescription thereof was shown in the following Table 1. The performance indexes of the buccal micro-effervescent tablet of each group, such as angle of repose, moisture absorption, hardness, friability and the like, were tested, and the test results were shown in Table 2.

TABLE 1

Prescription of the buccal micro-effervescent table

| Name of material | Prescription 1 | Prescription 2 | Prescription 3 | Prescription 4 | Prescription 5 | Prescription 6 | Prescription 7 | Prescription 8 | Prescription 9 | Prescription 10 |
|---|---|---|---|---|---|---|---|---|---|---|
| maltitol | 40 | 140 | 170 | 204.5 | 250.9 | 250.9 | 260 | 260 | / | / |
| lactose | 195.2 | 89.5 | 39.3 | / | / | / | / | / | 233.5 | 209.3 |
| vitamin C | 40 | 40 | 42 | 42 | 42 | 42 | 40 | 42 | 40 | 42 |
| anhydrous citric acid | 56 | 56 | 70 | 70 | 45.2 | 47 | 45.9 | 41.1 | 56 | 70 |
| sodium bicarbonate | 56 | 56 | 65 | 65 | 45 | 48 | 42 | 40 | 56 | 65 |
| essence | 6.8 | 6.8 | 6.8 | 6.8 | 6 | 6 | 6 | 6 | 6.8 | 6.8 |
| sucralose | 0.1 | 0.1 | 0.1 | 0.1 | 0.1 | 0.1 | 0.1 | 0.1 | 0.1 | 0.1 |
| aspartame | 2.4 | 2.4 | 2.4 | 2.4 | 1.6 | 1.6 | 1.6 | 1.6 | 2.4 | 1.6 |
| stevioside | 1.2 | 1.2 | 1.2 | 1.2 | 1.2 | 1.2 | 1.2 | 1.2 | 1.2 | 1.2 |
| magnesium stearate | 4 | 6 | 3.2 | 3.2 | 6 | 3.2 | 3.2 | 6 | 4 | 4 |
| silicon dioxide | / | 2 | / | 2 | 2 | / | / | 2 | / | / |
| Total amount of each tablet | 400 | 400 | 400 | 400 | 400 | 400 | 400 | 400 | | |

TABLE 2

Test results of performance index of the buccal micro-effervescent tablet

| Performance Index | Prescription 1 | Prescription 2 | Prescription 3 | Prescription 4 | Prescription 5 | Prescription 6 | Prescription 7 | Prescription 8 | Prescription 9 | Prescription 10 |
|---|---|---|---|---|---|---|---|---|---|---|
| Sense | Smooth | Smooth | Smooth | Smooth | Smooth | Sticking, rough surface | Sticking, rough surface | Sticking, rough surface | Smooth | Smooth |
| Angle of repose | 38° | 37° | 39° | 36° | 36° | 40° | 41° | 36° | 39 | 39 |
| Whether the production was successfully completed | Successfully completed | Successfully completed | Successfully completed | Successfully completed | Successfully completed | There was moisture absorption, sticking occurred during compressing for a | There was moisture absorption, sticking occurred during compressing, and the | There was moisture absorption, sticking occurred during compressing for a | Successfully completed | Successfully completed |

TABLE 2-continued

Test results of performance index of the buccal micro-effervescent tablet

| Performance Index | Prescription 1 | Prescription 2 | Prescription 3 | Prescription 4 | Prescription 5 | Prescription 6 | Prescription 7 | Prescription 8 | Prescription 9 | Prescription 10 |
|---|---|---|---|---|---|---|---|---|---|---|
| | | | | | | long time, and the production could not be successfully completed | production could not be successfully completed | long time, and the production could not be successfully completed | | |
| Hardness (kg/cm$^2$) | 5-8 | 5-8 | 5-8 | 5-8 | 5-8 | 5-8 | 5-8 | 5-8 | 5-8 | 5-8 |
| Friability (%) | 0.11 | 0.1 | 0.11 | 0.17 | 0.18 | 0.24 | 0.29 | 0.38 | 0.23 | 0.22 |

From the above test results, it could be known that in the present test example, as the amount of maltitol used increased, the moisture absorption of the prescription was enhanced, and accordingly the sticking phenomenon was liable to occur during compressing tablet; and magnesium stearate could improve the sticking phenomenon caused by moisture absorption of the prescription.

Test Example 2

On the basis that the sugar alcohol was a combination of sorbitol and lactose, the buccal micro-effervescent tablets of vitamin C were prepared by adjusting the ratio of sorbitol and lactose. The prescription thereof was shown in the following Table 3. The performance indexes of the buccal micro-effervescent tablet of each group, such as angle of repose, moisture absorption, hardness, friability and the like, were tested, and the test results were shown in Table 4.

TABLE 3

Prescription of the buccal micro-effervescent tablet

| Name of material | Prescription 1 | Prescription 2 | Prescription 3 | Prescription 4 | Prescription 5 | Prescription 6 | Prescription 7 | Prescription 8 | Prescription 9 | Prescription 10 |
|---|---|---|---|---|---|---|---|---|---|---|
| sorbitol | 40 | 80 | 120 | 120 | 140 | 181.7 | 219.5 | 219.5 | / | / |
| lactose | 166.5 | 126.5 | 101.5 | 89.3 | 54.5 | 42.6 | / | / | 209.3 | 196.5 |
| vitamin C | 40 | 40 | 40 | 42 | 42 | 42 | 40 | 42 | 40 | 42 |
| anhydrous citric acid | 70 | 70 | 60 | 70 | 75 | 60 | 64.4 | 60 | 70 | 75 |
| sodium bicarbonate | 65 | 65 | 60 | 65 | 70 | 60 | 62.4 | 60 | 65 | 70 |
| essence | 6.8 | 6.8 | 6.8 | 6.8 | 6.8 | 6.8 | 6.8 | 6.8 | 6.8 | 6.8 |
| sucralose | 0.1 | 0.1 | 0.1 | 0.1 | 0.1 | 0.1 | 0.1 | 0.1 | 0.1 | 0.1 |
| aspartame | 2.4 | 2.4 | 2.4 | 2.4 | 2.4 | 2.4 | 2.4 | 2.4 | 2.4 | 2.4 |
| stevioside | 1.2 | 1.2 | 1.2 | 1.2 | 1.2 | 1.2 | 1.2 | 1.2 | 1.2 | 1.2 |
| magnesium stearate | 6 | 6 | 6 | 3.2 | 6 | 3.2 | 3.2 | 6 | 3.2 | 6 |
| silicon dioxide | 2 | 2 | 2 | / | 2 | / | / | 2 | 2 | / |
| Total amount of each tablet | 400 | 400 | 400 | 400 | 400 | 400 | 400 | 400 | 400 | 400 |

TABLE 4

Test results of performance index of the buccal micro-effervescent tablet

| Performance Index | Prescription 1 | Prescription 2 | Prescription 3 | Prescription 4 | Prescription 5 | Prescription 6 | Prescription 7 | Prescription 8 | Prescription 9 | Prescription 10 |
|---|---|---|---|---|---|---|---|---|---|---|
| Sense | Smooth | Smooth | Smooth | Smooth | Smooth | Sticking, rough surface | Sticking, rough surface | Sticking, rough surface | Smooth | Smooth |
| Angle of repose | 36° | 36° | 35° | 39° | 36° | 40° | 42° | 37° | 39 | 38 |

TABLE 4-continued

Test results of performance index of the buccal micro-effervescent tablet

| Performance Index | Prescription 1 | Prescription 2 | Prescription 3 | Prescription 4 | Prescription 5 | Prescription 6 | Prescription 7 | Prescription 8 | Prescription 9 | Prescription 10 |
|---|---|---|---|---|---|---|---|---|---|---|
| Whether the production was successfully completed | Successfully completed | Successfully completed | Successfully completed | Successfully completed | Successfully completed | There was moisture absorption, sticking occurred during compressing for a long time, and the production could not be successfully completed | There was moisture absorption, severe sticking occurred during compressing, and the production could not be successfully completed | There was moisture absorption, sticking occurred during compressing for a long time, and the production could not be successfully completed | Successfully completed | Successfully completed |
| Hardness (kg/cm$^2$) | 5-8 | 5-8 | 5-8 | 5-8 | 5-8 | 5-8 | 5-8 | 5-8 | 5-8 | 5-8 |
| Friability (%) | 0.15 | 0.14 | 0.14 | 0.12 | 0.16 | 0.12 | 0.16 | 0.09 | 0.21 | 0.19 |

From the above test results, it could be known that in the present test example, as the amount of sorbitol used increased, the moisture absorption of the prescription was enhanced, and accordingly the sticking was liable to occur during compressing tablet; and magnesium stearate could improve the sticking phenomenon caused by the moisture absorption of the prescription.

Test Example 3

On the basis that the sugar alcohol is a combination of isomaltitol and lactose, the buccal micro-effervescent tablets of vitamin C were prepared by adjusting the ratio of isomaltitol and lactose. The prescription thereof was shown in the following Table 5. The performance indexes of the buccal micro-effervescent tablet of each group, such as angle of repose, moisture absorption, hardness, friability and the like, were tested, and the test results were shown in Table 6.

TABLE 5

Prescription of the buccal micro-effervescent tablet

| Name of material | Prescription 1 | Prescription 2 | Prescription 3 | Prescription 4 | Prescription 5 | Prescription 6 | Prescription 7 | Prescription 8 |
|---|---|---|---|---|---|---|---|---|
| isomaltitol | / | / | 80 | 140 | 205.4 | 230 | 260 | 260 |
| lactose | 237.5 | 198.7 | 129.1 | 64.3 | / | / | / | / |
| vitamin C | 42 | 42 | 42 | 42 | 42 | 42 | 42 | 42 |
| anhydrous citric acid | 61 | 75 | 70 | 70 | 70 | 56.8 | 45 | 40.2 |
| sodium bicarbonate | 45 | 65 | 65 | 65 | 65 | 52.7 | 39.3 | 39.3 |
| essence | 6 | 6.8 | 6.8 | 6.8 | 6.8 | 6.8 | 6.8 | 6.8 |
| sucralose | 0.1 | 0.1 | 0.1 | 0.1 | 0.1 | 0.1 | 0.1 | 0.1 |
| aspartame | 3.2 | 3.2 | 2.4 | 2.4 | 2.4 | 2.4 | 2.4 | 2.4 |
| stevioside | 1.2 | 1.2 | 1.4 | 1.4 | 1.2 | 1.2 | 1.2 | 1.2 |
| magnesium stearate | 2 | 6 | 3.2 | 6 | 6 | 6 | 3.2 | 6 |
| silicon dioxide | 2 | 2 | / | 2 | 2 | 2 | / | 2 |
| Total amount of each tablet | 400 | 400 | 400 | 400 | 400 | 400 | 400 | 400 |
| Test results | Smooth sense, angle of repose of 36°, and successful completion of production. Hardness: 5-8 kg/cm$^2$, | Smooth sense, angle of repose of 37°, and successful completion of production. Hardness: 5-8 kg/cm$^2$, | Smooth sense, angle of repose of 39°, and successful completion of production. Hardness: 5-8 kg/cm$^2$, | Smooth sense, angle of repose of 36°, and successful completion of production. Hardness: 5-8 kg/cm$^2$, | Smooth sense, angle of repose of 36°, and successful completion of production. Hardness: 5-8 kg/cm$^2$, | The angle of repose was 35°, there was moisture absorption, sticking occurred during compressing for a | The angle of repose was 40°, there was moisture absorption, sticking occurred during compressing, and the | The angle of repose was 36°, there was moisture absorption, sticking occurred during compressing for a |

TABLE 5-continued

Prescription of the buccal micro-effervescent tablet

| Name of material | Prescription 1 | Prescription 2 | Prescription 3 | Prescription 4 | Prescription 5 | Prescription 6 | Prescription 7 | Prescription 8 |
|---|---|---|---|---|---|---|---|---|
| | Friability: 0.23% | Friability: 0.21% | Friability: 0.18% | Friability: 0.15% | Friability: 0.23% | long time, and the production could not be successfully completed. Hardness: 5-8 kg/cm$^2$, Friability: 0.15% | production could not be successfully completed. Hardness: 5-8 kg/cm$^2$, Friability: 0.16% | long time, and the production could not be successfully completed. Hardness: 5-8 kg/cm$^2$, Friability: 0.17% |

TABLE 6

Test results of performance index of the buccal micro-effervescent tablet

| Performance Index | Prescription 1 | Prescription 2 | Prescription 3 | Prescription 4 | Prescription 5 | Prescription 6 | Prescription 7 | Prescription 8 |
|---|---|---|---|---|---|---|---|---|
| Sense | Smooth | Smooth | Smooth | Smooth | Smooth | Sticking, rough surface | Sticking, rough surface | Sticking, rough surface |
| Angle of repose | 36° | 37° | 39° | 36° | 36° | 35° | 40° | 36° |
| Whether the production was successfully completed | Successfully completed | Successfully completed | Successfully completed | Successfully completed | Successfully completed | There was moisture absorption, sticking occurred during compressing for a long time, and the production could not be successfully completed | There was moisture absorption, sticking occurred during compressing, and the production could not be successfully completed | There was moisture absorption, sticking occurred during compressing, and the production could not be successfully completed |
| Hardness (kg/cm$^2$) | 5-8 | 5-8 | 5-8 | 5-8 | 5-8 | 5-8 | 5-8 | 5-8 |
| Friability (%) | 0.15 | 0.21 | 0.18 | 0.15 | 0.23 | 0.15 | 0.16 | 0.17 |

From the above test results, it could be known that in the present test example, as the amount of isomaltitol used increased, the moisture absorption of the prescription was enhanced, and accordingly the sticking phenomenon was liable to occur during compressing tablet; and magnesium stearate could improve the sticking phenomenon caused by the moisture absorption of the prescription.

Test Example 4

Five sensory indexes including appearance, odour, mouthfeel, being or not being convenient to eat and novelty of the products of Example 1 and Comparative example 1 of the present invention were evaluated by 14 senior sensory assessors, each index had a full score of 5, and the total full score of five sensory indexes was 25. The scoring results were averaged. The scoring results of sensory index were as follows.

TABLE 7

Scoring results of sensory evaluation of the buccal micro-effervescent tablets of Example 1

| No. of assessor | Appearance | Odour | Mouthfeel | Being or not being convenient to eat | Novelty | Total score |
|---|---|---|---|---|---|---|
| 1 | 4 | 4 | 4 | 5 | 5 | 22 |
| 2 | 3 | 4 | 4 | 5 | 5 | 21 |
| 3 | 4 | 4 | 4 | 4 | 4 | 20 |
| 4 | 4 | 3 | 3 | 5 | 5 | 20 |
| 5 | 4 | 3 | 4 | 4 | 4 | 19 |
| 6 | 3 | 4 | 4 | 5 | 5 | 21 |
| 7 | 2 | 4 | 4 | 4 | 4 | 18 |
| 8 | 3 | 4 | 5 | 5 | 5 | 22 |
| 9 | 4 | 3 | 3 | 5 | 4 | 19 |
| 10 | 3 | 3 | 4 | 5 | 5 | 20 |
| 11 | 3 | 4 | 4 | 4 | 4 | 19 |
| 12 | 2 | 4 | 4 | 5 | 5 | 20 |
| 13 | 2 | 3 | 3 | 5 | 4 | 17 |
| 14 | 2 | 3 | 4 | 4 | 5 | 18 |
| Average Score | 3.07 | 3.57 | 3.86 | 4.64 | 4.57 | 19.71 |

TABLE 8

Scoring results of sensory evaluation of effervescent tablets of Comparative example 1

| No. of assessor | Appearance | Odour | Mouthfeel | Being or not being convenient to eat | Novelty | Total score |
|---|---|---|---|---|---|---|
| 1 | 4 | 4 | 4 | 4 | 4 | 20 |
| 2 | 3 | 4 | 4 | 3 | 4 | 18 |
| 3 | 4 | 4 | 4 | 3 | 3 | 18 |
| 4 | 3 | 3 | 3 | 4 | 3 | 16 |
| 5 | 3 | 2 | 3 | 3 | 3 | 14 |
| 6 | 3 | 3 | 3 | 3 | 4 | 16 |
| 7 | 3 | 3 | 4 | 4 | 3 | 17 |
| 8 | 2 | 4 | 4 | 3 | 3 | 16 |
| 9 | 4 | 3 | 3 | 4 | 4 | 18 |
| 10 | 2 | 2 | 3 | 3 | 3 | 13 |
| 11 | 3 | 3 | 3 | 4 | 3 | 16 |
| 12 | 2 | 4 | 4 | 3 | 4 | 17 |
| 13 | 4 | 2 | 4 | 3 | 3 | 16 |
| 14 | 4 | 3 | 3 | 3 | 4 | 17 |
| Average Score | 3.14 | 3.14 | 3.5 | 3.36 | 3.43 | 16.57 |

From the above results, it could be known that the product of Example 1 could be designed to have a cute appearance, had a good aroma, was sour, sweet and palatable when dissolved in mouth, was very convenient to eat, was novel, could be designed to be a snack, and had a high acceptability.

The product of Comparative Example 1 had a common appearance, was in a common tablet shape, had a good aroma, was sour, sweet and palatable when dissolved in water, and was convenient to eat. The package thereof was designed to be a medicine, and the acceptability thereof was common. In Comparative Example 1, the amount of acid and alkali used was large, the effervescence was violent, and the mouthfeel was not good.

Test Example 5

The sticking phenomenon of the products of examples 1-12 and comparative examples 1-4 was observed, and the mouthfeel thereof was evaluated and described.

The results were as follows.

TABLE 9

Sticking performance and mouthfeel of each effervescent tablet

| Test items | Sticking Phenomenon | Mouthfeel |
|---|---|---|
| Example 1 | Not easy to cause sticking | Good mouthfeel, pleasant aroma |
| Example 2 | Not easy to cause sticking | Good mouthfeel, pleasant aroma |
| Example 3 | Not easy to cause sticking | Good mouthfeel, pleasant aroma |
| Example 4 | Not easy to cause sticking | Good mouthfeel, pleasant aroma |
| Example 5 | Not easy to cause sticking | Good mouthfeel, pleasant aroma |
| Example 6 | Not easy to cause sticking | Good mouthfeel, pleasant aroma |
| Example 7 | Not easy to cause sticking | Good mouthfeel, pleasant aroma |
| Example 8 | Not easy to cause sticking | Good mouthfeel, pleasant aroma |
| Example 9 | Not easy to cause sticking | Good mouthfeel, pleasant aroma |
| Example 10 | Not easy to cause sticking | Good mouthfeel, pleasant aroma |
| Example 11 | Not easy to cause sticking | Good mouthfeel, pleasant aroma |
| Example 12 | Not easy to cause sticking | Good mouthfeel, pleasant aroma |
| Comparative Example 1 | Generating heat causes sticking during compression. | Good mouthfeel, pleasant aroma |
| Comparative Example 2 | Generating heat causes sticking during compression. | Good mouthfeel, pleasant aroma |
| Comparative Example 3 | Not easy to cause sticking | Rough mouthfeel, surface of the tablet being not smooth when buccally taken |
| Comparative Example 4 | Not easy to cause sticking | Insufficient fragrance and aroma being not obvious |

The foregoing is only a part of the embodiments of the present invention, and it should be noted that, for those skilled in the art, various modifications can be made without departing from the principle of the present invention, and these should also be construed as the scope of the present invention.

What is claimed is:

1. A buccal micro-effervescent tablet comprising:
    a nutrient, wherein the nutrient is Vitamin C;
    a sugar alcohol, wherein the sugar alcohol is a combination of lactose and maltitol and wherein the ratio of lactose to maltitol is 1:2.2-1:4.5 in parts by weight;
    an acid source, wherein the acid source is citric acid, tartaric acid, fumaric acid, malic acid, or any combination thereof;
    an alkali source, wherein the alkali source is sodium bicarbonate, sodium carbonate, potassium bicarbonate, potassium carbonate or any combination thereof;
    a magnesium stearate;
    an essence; and
    a sweetening agent, wherein the sweetening agent is a combination of sucralose, aspartame and stevioside,
    wherein the buccal micro-effervescent tablet comprises in parts by weight: 8-12 parts of the nutrient, 10-80 parts of the sugar alcohol, 11-19 parts of the acid source, 11-18 parts of the alkali source, 0.1-3 parts of the magnesium stearate, 1-5 parts of the essence and 0.1-3 parts of the sweetening agent.

2. The buccal micro-effervescent tablet according to claim 1, wherein the buccal micro-effervescent tablet comprises in parts by weight:
    10-11 parts of the nutrient, 48-63 parts of the sugar alcohol, 11-19 parts of the acid source, 11-18 parts of the alkali source, 0.8-1.5 parts of the magnesium stearate, 1.5-2 parts of the essence, and 0.2-1.2 parts of the sweetening agent.

3. The buccal micro-effervescent tablet according to claim 1, wherein the buccal micro-effervescent tablet further comprises silicon dioxide, the weight ratio of the silicon dioxide in the buccal micro-effervescent tablet is 0.1%-1%.

4. A method for preparing the buccal micro-effervescent tablet according to claim 1, comprising:
    mixing the nutrient, the sugar alcohol, the acid source, the alkali source, the magnesium stearate, the essence, and the sweetening agent to obtain a mixture; and
    compressing the mixture into a tablet.

5. A buccal micro-effervescent tablet comprising in parts by weight: 9.8-48.8 parts lactose, 10-42.5 parts maltitol, 10-10.5 parts vitamin C, 14-17.5 parts anhydrous citric acid, 14-16.25 parts sodium bicarbonate, 1.7-2 parts essence, 0.025-0.03 parts sucralose, 0.12-0.6 parts aspartame, 0.05-0.3 parts stevioside, 0.8-1.5 parts magnesium stearate, and optionally further comprising 0.1-1 parts silicon dioxide.

* * * * *